United States Patent
Bose et al.

(10) Patent No.: US 9,987,397 B2
(45) Date of Patent: Jun. 5, 2018

(54) WEAR RESISTANT LOW FRICTION COEFFICIENT SURFACES FOR JOINT AND BONE REPLACEMENT MATERIALS AND DEVICES

(71) Applicant: WASHINGTON STATE UNIVERSITY, Pullman, WA (US)

(72) Inventors: Susmita Bose, Pullman, WA (US); Amit Bandyopadhyay, Pullman, WA (US)

(73) Assignee: Washington State University, Pullman, WA (US)

(*) Notice: Subject to any disclaimer, the term of this patent is extended or adjusted under 35 U.S.C. 154(b) by 241 days.

(21) Appl. No.: 14/378,160

(22) PCT Filed: Feb. 11, 2013

(86) PCT No.: PCT/US2013/025534
§ 371 (c)(1),
(2) Date: Aug. 12, 2014

(87) PCT Pub. No.: WO2013/122862
PCT Pub. Date: Aug. 22, 2013

(65) Prior Publication Data
US 2015/0004209 A1    Jan. 1, 2015

Related U.S. Application Data

(60) Provisional application No. 61/598,141, filed on Feb. 13, 2012.

(51) Int. Cl.
| | |
|---|---|
| *A61L 31/14* | (2006.01) |
| *A61L 31/02* | (2006.01) |
| *A61F 2/30* | (2006.01) |
| *A61L 27/04* | (2006.01) |
| *A61L 27/06* | (2006.01) |
| *A61L 27/32* | (2006.01) |
| *A61L 27/50* | (2006.01) |

(52) U.S. Cl.
CPC .............. *A61L 31/14* (2013.01); *A61F 2/30* (2013.01); *A61F 2/3094* (2013.01); *A61F 2/30767* (2013.01); *A61L 27/04* (2013.01); *A61L 27/06* (2013.01); *A61L 27/32* (2013.01); *A61L 27/50* (2013.01); *A61L 31/022* (2013.01); *A61F 2002/3097* (2013.01); *A61F 2002/30673* (2013.01); *A61F 2002/30934* (2013.01); *A61L 2400/10* (2013.01)

(58) Field of Classification Search
None
See application file for complete search history.

(56) References Cited

U.S. PATENT DOCUMENTS

| | | | | |
|---|---|---|---|---|
| 4,663,060 | A | * 5/1987 | Holinski | .............. C10M 103/00 188/251 A |
| 5,370,694 | A | * 12/1994 | Davidson | .............. A61F 2/0077 623/23.6 |
| 5,976,190 | A | 11/1999 | Anhalt et al. | |
| 6,709,463 | B1 | 3/2004 | Pope et al. | |
| 8,029,917 | B2 | * 10/2011 | Spain | .................. A61F 2/30767 420/501 |
| 2009/0093881 | A1 | 4/2009 | Bandyopadhyay et al. | |

OTHER PUBLICATIONS

Roy et al., Laser processing of bioactive tricalcium phosphate coating on titanium for load-bearing implants, Acta Biomaterialia (2008), vol. 4, pp. 324-333.*
Alternative Methods of Metal Deposition (1997).*

* cited by examiner

*Primary Examiner* — Hasan S Ahmed
*Assistant Examiner* — Frank Choi
(74) *Attorney, Agent, or Firm* — Liang IP, PLLC

(57) ABSTRACT

A metal matrix has a biocompatible solid lubricant in at least a portion of its surface and the solid lubricant functions to protect the interior of the metal matrix and minimize the friction coefficient and related wear induced damage at the articulating surface of the metal device. The lubricated biocompatible metal device is made of materials compatible for in vivo and ex vivo applications in order to minimize wear induced degradation as well as metal ion release. The lubricated biocompatible metal device is suited for use as medical implants.

23 Claims, 10 Drawing Sheets

WEAR RESISTANT LOW FRICTION COEFFICIENT SURFACES FOR JOINT AND BONE REPLACEMENT MATERIALS AND DEVICES

BACKGROUND OF THE INVENTION

The advancement of enhanced materials for the use of medical implants, such as joint prostheses, has immensely improved the quality of life for many people over the past century. Devices such as artificial hips, knees, shoulders and other devices have allowed people who would otherwise have suffered from chronic pain and physical limitation to live active, comfortable lives. The development of such devices has confronted scientists and engineers with many technical challenges, such as in the area of materials science engineering, where various biocompatible materials with different physical and mechanical properties are bonded to each other in order to achieve optimal implant performance.

However, over the past several decades, surgical implants have been manufactured by making a near-net-shape part by forging or casting followed by machining and finishing operations for the desired surface. These operations require expensive tooling and only make sense for large volume production. Using similar practice, manufacturing of patient matched or low volume implants become a cost intensive effort and are rarely practiced. Other challenges such as difficulty in machining of titanium alloys due to high strength, low ductile yield make it even more expensive to machine titanium (Ti) based implants commercially. In addition, conventional manufacturing technologies are energy intensive, produce significant amounts of materials waste and cannot produce devices with functional gradation.

Additive manufacturing (AM) represents a new option for production of orthopedic implants. Although AM requires final machining or hand finishing, it allows significant flexibility towards manufacturing low-volume, complex implants. U.S. Pat. No. 7,666,522 to Justin et al., issued on Feb. 23, 2010, and which is incorporated herein by reference, discloses a method for purportedly depositing a hard wear resistant surface onto a porous or non-porous base material of a medical implant. The wear resistant surface of the medical implant device in Justin et al. may be formed by a Laser Based Metal Deposition (LBMD) method such as Laser Engineered Net Shaping (LENS).

Materials used for such devices must not only be non-corrosive, but must also be sufficiently resilient (having high tensile and compressive strength), and hard (having sufficient wear resistance). Since a device such as an artificial joint must undergo a great number of cycles of wear during the lifetime of the host patient, such devices must also possess great fatigue properties.

Justin et al. purportedly addresses the need for a device, such as an artificial joint, which can take advantage of the properties of a first material, such as the porosity of porous tantalum (Ta) or Ti, and also take advantage of the properties of a second material, such as the hardness of a material like alloys of cobalt and chrome (Co—Cr), for use in a bearing environment such as a ball or socket of a joint. According to Justin et al., such a device would preferably not exhibit any delamination between the two materials and would not experience any galvanic corrosion. In addition, Justin et al. discloses that such a device would also preferably not diminish the porosity of the porous material due to the flow of the other material thereinto.

Typically for load-bearing biomedical devices, Co and Cr materials are used for construction of most devices, in particular the CoCrMo alloy. However, concerns related to higher amounts of Co and Cr ion release in recent years prompted the U.S. Food and Drug Administration in 2010 to direct leading implant manufacturers to conduct post-market studies of their devices to determine whether a high level of metallic debris was being released into a patient's body.

Though metal-on-metal devices may offer greater motion, higher stability and greater than 99% reduction in wear debris compared to ultra high molecular weight polyethylene (UHMWPE) components in lab experiments, concerns are growing related to excess metallic ions being released in the body that can cause metallosis, severe tissue and bone damage. Accordingly, there is a need to address the problems in the prior art.

SUMMARY OF THE INVENTION

The invention relates to lubrication of a metal matrix by addition of biocompatible softer materials, such as at least one solid lubricant, and a method for lubricating and producing the same. The soft material, such as a dry or solid lubricant, embedded into the device minimizes the friction coefficient and resultant wear at the articulating surface of the lubricated metal device. The biocompatible lubricated metal device is made of materials compatible for in vivo and ex vivo applications in order to minimize wear induced degradation and to minimize metal ion release during use. The biocompatible lubricated metal device is suited for use as medical implants, as well as in industrial and other applications, and offers safe composite properties, including biodegradable wear debris in vivo.

DETAILED DESCRIPTION OF THE INVENTION

It is understood that specific embodiments are provided as examples to teach the broader inventive concept, and one of ordinary skill in the art can easily apply the teachings of the present disclosure to other methods and systems. Also, it is understood that the methods and systems discussed in the present disclosure include some conventional structures and/or steps. Since these structures and steps are well known in the art, they will only be discussed in a general level of detail. Furthermore, reference numbers are repeated throughout the drawings for the sake of convenience and example, and such repetition does not indicate any required combination of features or steps throughout the drawings.

Figure 1:
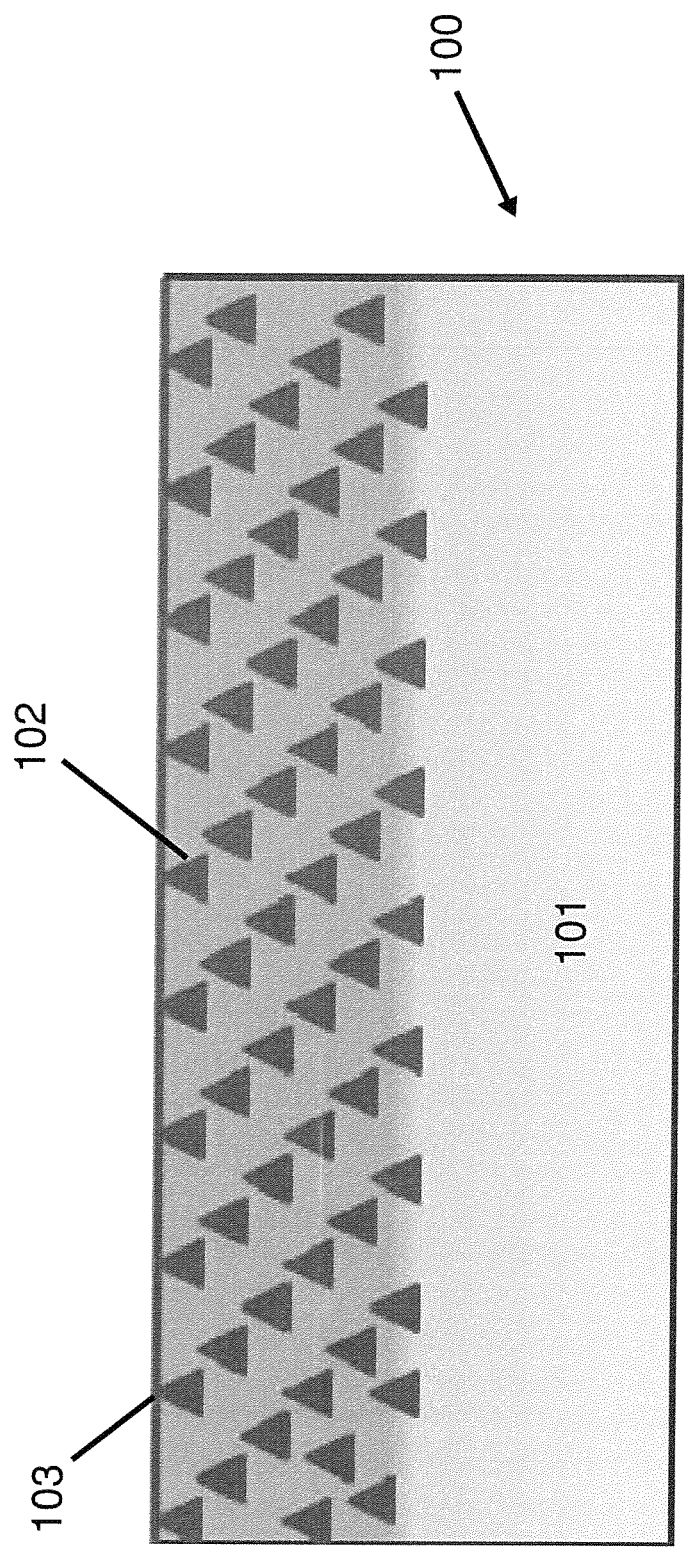
FIG. 1 illustrates a cross-sectional view of an exemplary lubricated biocompatible metal device according to the present invention.

FIG. 1 illustrates a cross-sectional view of an exemplary lubricated biocompatible metal device 100 according to the present invention. The lubricated metal device 100 may be a solid lubricant 102 embedded into a metal matrix 101 in order to increase hardness and improve wear resistance during use of the device 100. The solid lubricant 102 may cover all, most, or only a specified portion of the surface of metal matrix 101 and functions to reduce the wear of the base metal while the part is in service.

In an exemplary embodiment, the lubricated biocompatible metal device 100 may be a titanium (Ti) and calcium phosphate (CaP) composition. For example, the CaP may be composed of hydroxyapatite ($Ca_{10}(PO_4)_6(OH)_2$), tri calcium phosphate ($Ca_3(PO_4)_2$), a combination of both or a combination of other forms of CaP, including, but not limited to, amorphous CaP. Given such a composition (Ti—CaP), the solid-lubricated surface 103 will be primarily CaP, a ceramic which is a solid lubricant 102 and which functions to reduce the metal (Ti) ion release from the metal device 100. Moreover, when a high concentration of CaP is embedded (e.g., between 5 to 25 weight % of CaP in Ti) in the metal matrix 101 of the preferred embodiment, this behavior will continue as the biocompatible device 100 is being used in service.

A solid lubricant 102, which may also be referred to as a dry lubricant, is a material, which despite being in the solid phase and a soft material, can reduce a friction coefficient and any related wear between two surfaces sliding against each other with or without the need for a liquid medium. A coefficient of friction is a dimensionless scalar value which describes the ratio of the force of friction between two bodies and the force pressing them together. In general, coefficients of friction range from near zero to greater than one. In the context of the present invention, solid lubricant 102 reduces the coefficient of friction to a level that is lower than if the solid lubricant was not present.

A solid lubricant 102 can shear easily along a certain plane when a load is applied. A common but non-limiting example of a solid lubricant 102 is mica or graphite, which because of its low strength along a Z direction in the basic crystallography, can protect another solid by creating a thin layer or film on top of the majority of the metal matrix 101. Under direct contact or wear, the solid lubricant's protective film or the solid-lubricated surface 103 contacts with the mating surface and slowly wears out with time, protecting the interior material of the metal matrix 101 and the biocompatible device 100.

In the practice of the invention, a solid-lubricated surface 103 is a reservoir of a solid lubricant 102 which protects the interior of the metal matrix 101 by continuously forming films during use to cover the entire surface or part of a surface of the metal matrix 101. As the films wear out, the surface 103 may be replenished with a solid lubricant 102 embedded in the metal matrix 101.

In general, most solid lubricants are soft materials that are weak along a certain crystallographic axis, but they can also be hard materials. An exemplary but non-limiting listing of the materials suitable as solid lubricants, includes the following: magnesium hydrosilicates family of materials (including but not limited to talc and olivine), carbon based materials such as graphite, molybdenum disulfide, tungsten disulfide, hexagonal boron nitride, calcium phosphate family of materials (including but not limited to hydroxyapatite, tri- and tetra-calcium phosphates), calcium carbonates and calcium sulphates with and without the addition of any dopants (in a preferred embodiment, between 0 to 50 wt. % to improve their biocompatibility and lubricity), alumina, lead zirconate titanate, and moon rock simulant. In addition, many other polymers show similar behavior which may be suitable as solid lubricants, including but not limited to teflon (i.e., polytetrafluroethelyne). In the composite form, solid lubricants may be isolated and fully adhered with the metal matrix material; in an alternative, solid lubricants may partially dissolve within the metal matrix material and create a local compositional gradient.

Figure 2:
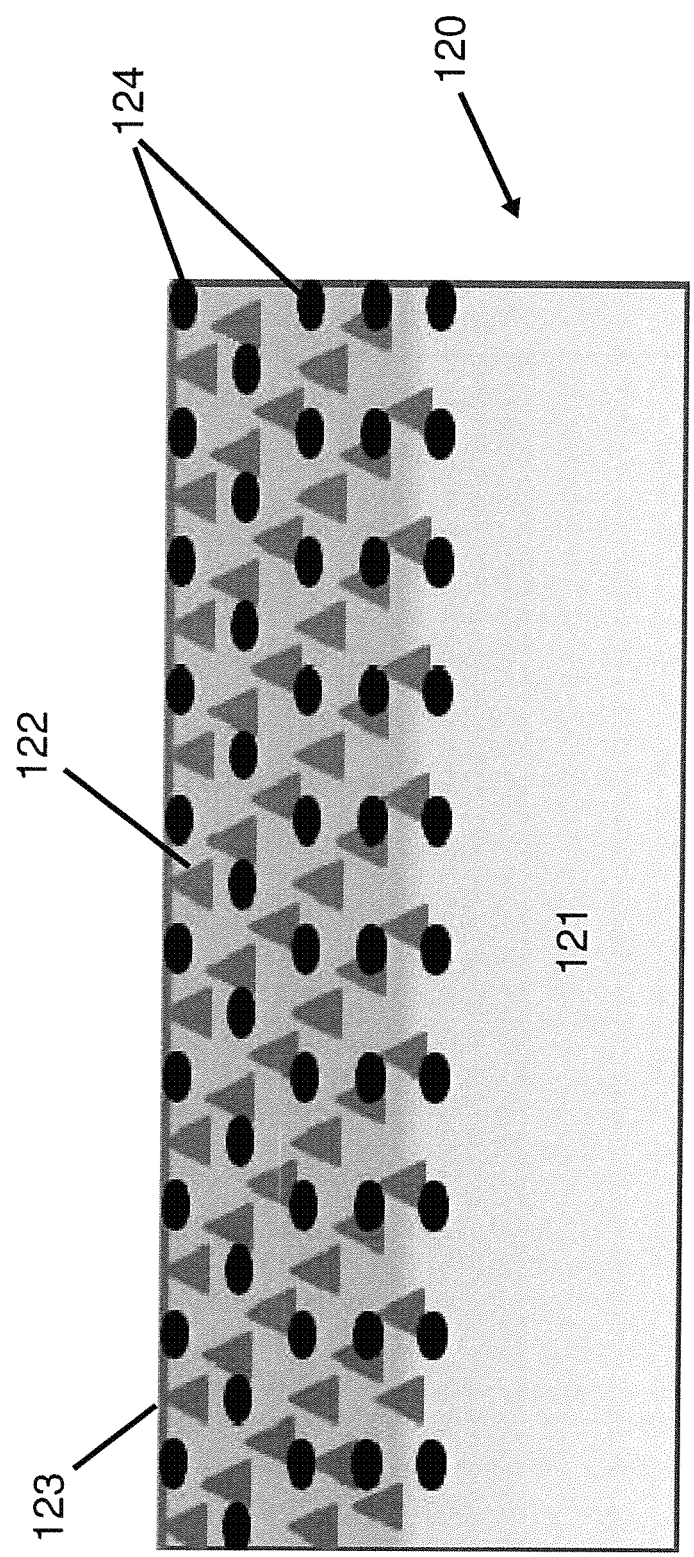
FIG. 2 illustrates a cross-sectional view of another exemplary lubricated biocompatible metal device according to the present invention.

FIG. 2 illustrates a cross-sectional view of an exemplary lubricated biocompatible metal device 120 according to the present invention. The lubricated biocompatible metal device 120 is similar to the lubricated biocompatible metal device 100 depicted in FIG. 1. However, FIG. 2 shows a device 120 with one or more additional solid lubricants 124 embedded into the metal matrix 121. The one or more additional solid lubricants 124 are composed of materials, which are dissimilar than the material of the solid lubricant 122. As discussed above with respect to FIG. 1, solid lubricants may be made of various suitable materials. Moreover, similar to FIG. 1, a solid lubricant 122 and additional solid lubricants 124 are embedded into a metal matrix 121 in order to form a protective solid-lubricated surface 123 covering a majority of the metal matrix 121 to reduce the wear of the base metal.

In an exemplary embodiment, the lubricated metal device 120 may be a Ti, CaP and carbon (C) composition. The carbon in such a composition may, for example, be in the form of graphite or carbon nanotube. Given such a composition (Ti—CaP—C), the solid-lubricated surface 123 will be primarily CaP and C; thus, reducing the metal (Ti) ion release. Moreover, because of the high concentration of CaP and C embedded in the metal matrix 121 of the preferred embodiment, this behavior will continue as the hiocompatible device 120 is being used in service.

In FIGS. 1 and 2, the metal matrix 101 or 121 may be constructed either completely or predominantly of a porous material, such as a porous matrix of Ta or Ta alloy, Ti or Ti alloy (e.g., Ti—6Al—4V, Ti—Ni, Ti6Al4V ELI), Titanium-Nickel alloys, Cobalt-Chrome alloys (e.g., CoCrMo alloy), etc.

Figure 3:
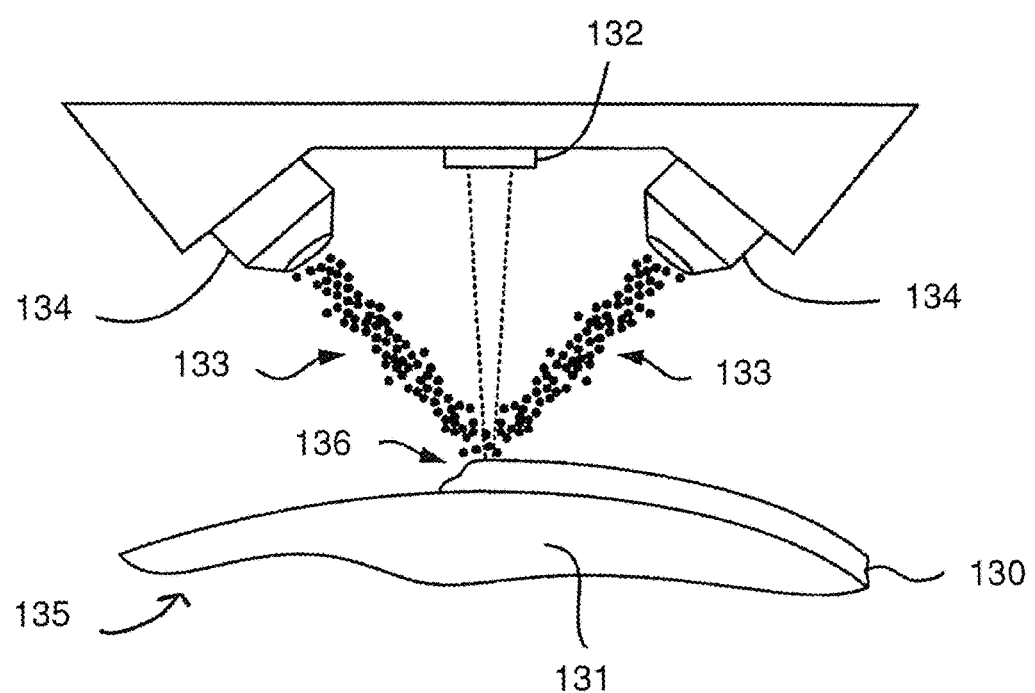
FIG. 3 shows an example of embedding of solid lubricants into a metal matrix by illustrating construction of a layer of a metal substrate according to a laser based metal deposition (LBMD) process.

FIG. 3, which is based on that depicted in U.S. Pat. No. 7,666,522 to Justin et al., shows an example of embedding of solid lubricants into a metal matrix by illustrating the construction of a layer 130 of the metal substrate 131 according to a laser based metal deposition (LBMD) process. An example of a LBMD process is Laser Engineered Net Shaping (LENS™), Sandia Corporation of Albuquerque, N. Mex., is described in U.S. Pat. No. 6,046,426 to Jeantette et al., issued on Apr. 4, 2000, and which is incorporated herein by reference. Initially, a layer is deposited directly on the metal substrate 131. Thereafter, subsequent layers can be deposited on previous layers in a controlled manner until a desired surface shape is formed. The material can be deposited for example as a powdered metal emitted from one or more nozzles. Alternatively, the material could be provided as a wire or as a foil, held in proximity to the base and heated with the laser.

As shown in FIG. 3, the layer 130 is formed first by depositing powdered material 133, such as but not limited to Ti or Ti alloy, onto the metal substrate 131, and immediately heating the material with a high power laser 132. A powdered material feeder (not illustrated) provides a uniform and continuous flow of a measured amount of powdered material 133 to the delivery system, or nozzle 134. The delivery system directs the powdered material 133 toward the metal substrate 131 and directs the powdered material 133 to flow in a converging, conical pattern whereby the apex of such converging, conical pattern intersects the minimum diameter of a focused laser beam (i.e. focus or focal plane) produced by a laser 132, such as, but not limited to, an Nd YAG laser, all of which is in close proximity to the surface of the metal matrix 135. This generates a melt zone 136, wherein a substantial portion of the powdered material 133 melts and is deposited on the surface of the metal substrate 131. A person having ordinary skill in the art will appreciate that such powdered material can melt either in flight or upon injection into a molten puddle of powdered material. By causing the metal substrate 131 to move relative to the delivery system or by moving the delivery system relative to the metal substrate 131, layers of molten deposited material can be deposited to form a net-shaped surface.

The layer 130 may be deposited as a single layer, or as multiple layers applied by successive passes of LBMD deposition. For instance in an embodiment of the invention, laminates of material, for example, metals and ceramics (e.g., one or more solid lubricants), can be formed to create the layer 130.

The LBMD deposition process is preferably performed in a controlled oxygen environment (not illustrated), preferably between 1 and 400 ppm of oxygen, which contains an inert gas to inhibit the formation of surface oxide in the deposition area. This reduces the amount of laser energy needed to achieve full melting of the powder material 133. Although deposition can be performed outside the controlled atmosphere chamber, the inert atmosphere will promote full density in the deposited structure and ultimately lead to improved strength of the applied surface material.

Please note that the heat used to apply each layer and/or the material composition can be adjusted with each pass to achieve a gradient of material properties if desired. As such, the layer 130 can also be formed to have a gradient of material qualities; for example, the layer 130 could be formed to become progressively harder toward its top surface. More detail about an exemplary embodiment with a harder zirconium based surface is provided below with respect to FIG. 6.

In addition, because of the rapid rate of heating and cooling, the applied material does not tend to excessively flow into porous material, thereby maintaining the desirable porous properties of the porous bulk portion of the device and a relatively small bonding zone between the porous material and the LBMD deposited material. This allows for a thin layer of LBMD deposited material to be deposited onto porous material. Because this layer of deposited material is thin, implants can be fabricated that are optimized in size to limit the amount of bone that must be removed to facilitate the bulk of the implant.

According to another embodiment, multi-layer structures such as that described above can be formed for coupling to another device such as a commercially available implant. For instance, such multi-layer structures can be fusion or diffusion bonded to implants that are made by traditional methods. A porous surface may advantageously be available for coupling to bone of a host patient.

Referring to FIG. 3, the metal matrix 135 may be constructed either completely or predominantly of a porous material, such as a porous matrix of Ta or Ta alloy, Ti or Ti alloy (e.g., Ti—6Al—4V, Ti—Ni, Ti6Al4V ELI), Titanium-Nickel alloys, Cobalt-Chrome alloys (e.g., CoCrMo alloy), etc. In addition, the metal matrix 135 may be made of a material including, but not limited to, aluminum, nickel, titanium, cobalt-chrome, tantalum, platinum, zirconium, niobium, stainless steel, and any alloys thereof.

An embodiment of the invention includes the deposition of a blended material in the form of a composite coating in multiple functionally graded layers, in order to enhance the coating performance. For instance, depositing a blended material may result in the lubricated metal device 120 as illustrated in FIG. 2, which shows a metal matrix 121 embedded with a solid lubricant 122 and one or more additional solid lubricants 124. For this embodiment, a powder material blend may be prepared by thoroughly mixing the constituent powders using ball milling or similar powder mixing techniques, and can then be applied to a metal matrix by an LBMD process or other suitable process.

Deposition parameters for the LBMD process include: laser power, scan speed, scan spacing, scan orientation, layer thickness, powder feed rate, and others. In a preferred embodiment, the deposition parameters would be a laser power between 150 W and 400 W, scan speeds between 5 mm/s and 25 mm/s, a powder feed rate in the range of 15 g/minute and 38 g/minute, and scan spacing between 0.76 mm and 1.27 mm.

Figure 4:
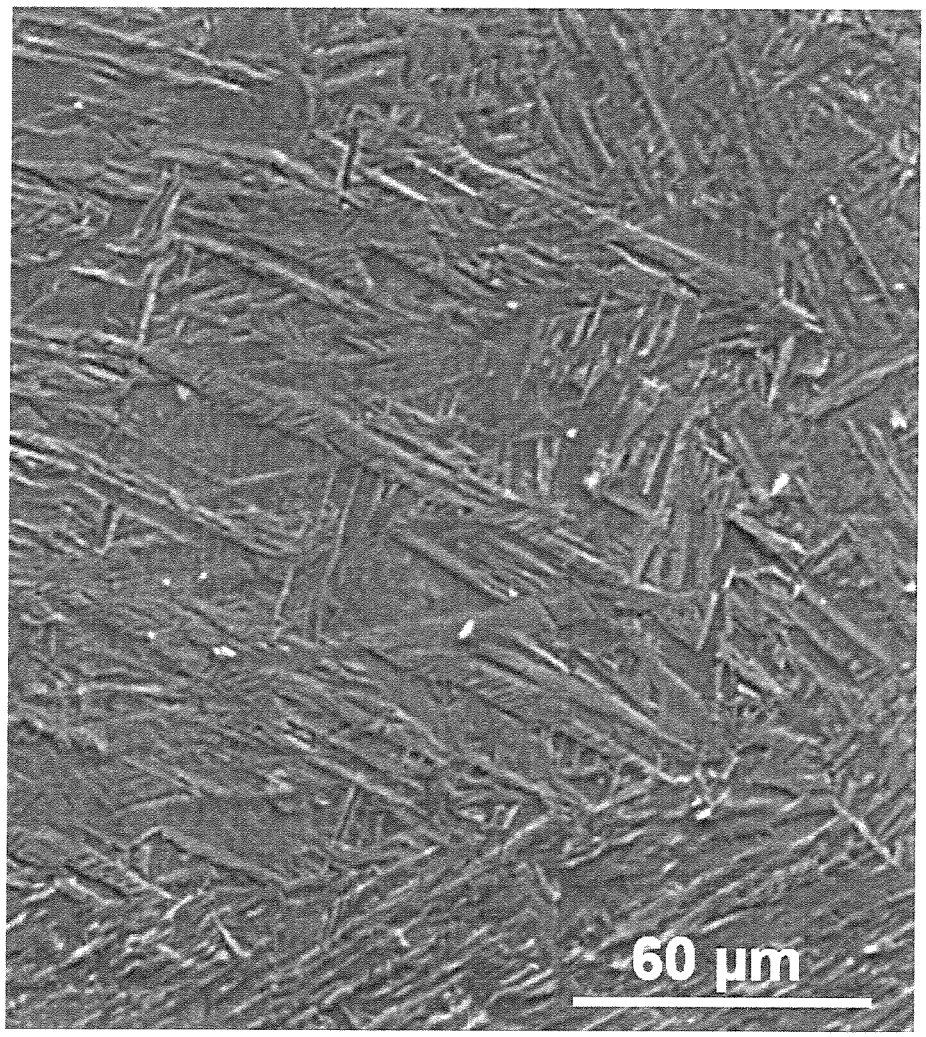
FIG. 4 illustrates experimental results of acicular a formed in fully dense commercially-pure Ti (cp-Ti).

As shown in FIG. 4, characteristic high solidification rates in materials results in fine microstructures in the final parts, where fine acicular a was formed in fully dense commercially-pure Ti (cp-Ti) experimental samples. Microstructural refinement can improve mechanical properties. For example, fine acicular alpha in Ti and Ti6Al4V alloy has been shown to provide the best fatigue resistance in the notched condition.

Figure 5:
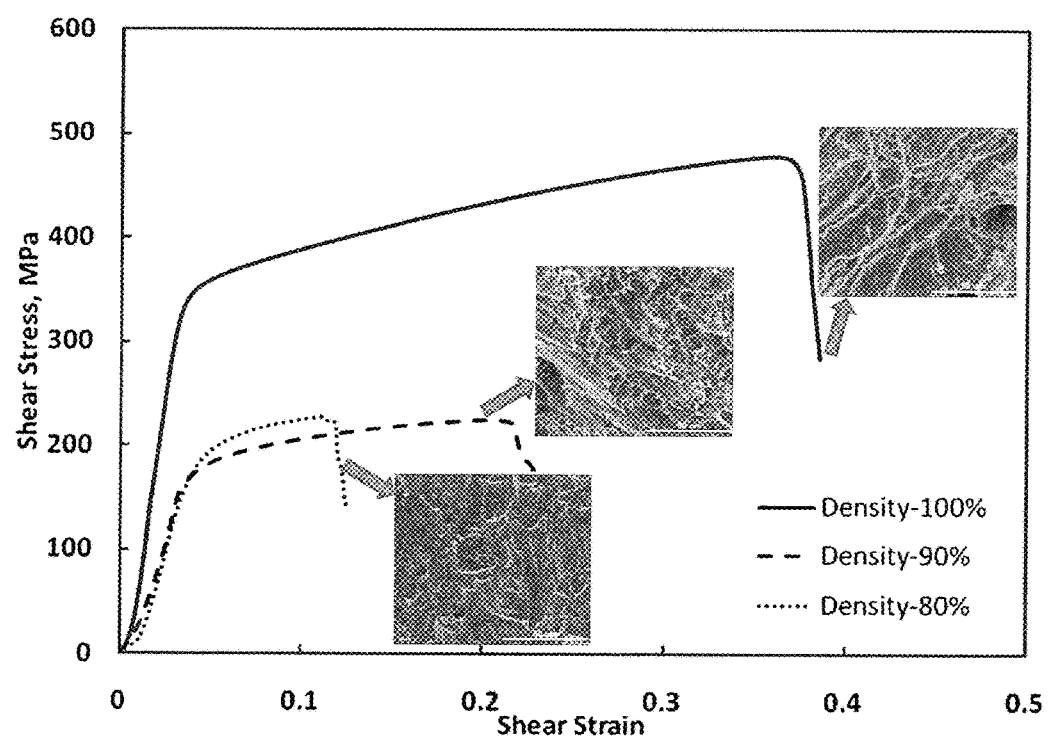
FIG. 5 is shear stress—shear strain curves obtained from a quasi-static torsional test of various processed Ti6Al4V alloys.

In reference to FIG. 5, a parametric study on quasi-static torsional deformation behavior of processed dense and porous Ti6Al4V alloy showed clear strain hardening and ductile failure mode in all experimental samples, suggesting the bonding between the particles is very strong even in porous samples.

Table 1 below provides a summary of the properties of exemplary, and non-limiting, LBMD processed materials:

TABLE 1

| Materials | Modulus (GPa) | Yield Strength (MPa) | In vitro biocompatibility | In vivo biocompatibility |
|---|---|---|---|---|
| cp-Ti | 115 ± 3 | 910 ± 32 | Non-toxic, excellent cell material interactions | Non-toxic and good tissue adherence and in-growth |
| Ti6Al4V | 104 ± 2 | 1014 ± 20 | | |

With respect to the fatigue behavior of these experimental samples, a compression-compression (C-C) fatigue testing was conducted on processed dense and porous cp-Ti and Ti6Al4V. Cylindrical samples were fatigue tested at room temperature under C-C mode using a servo-hydraulic Instron™ testing system. Samples were tested up to 106 cycles at a frequency of 15 Hz and stress ratio (R=minimum/ aximum stress) of 0.1. The samples did not show any fatigue degradation up to 106 cycles up to a stress of 125% of yield strength.

Figure 6:
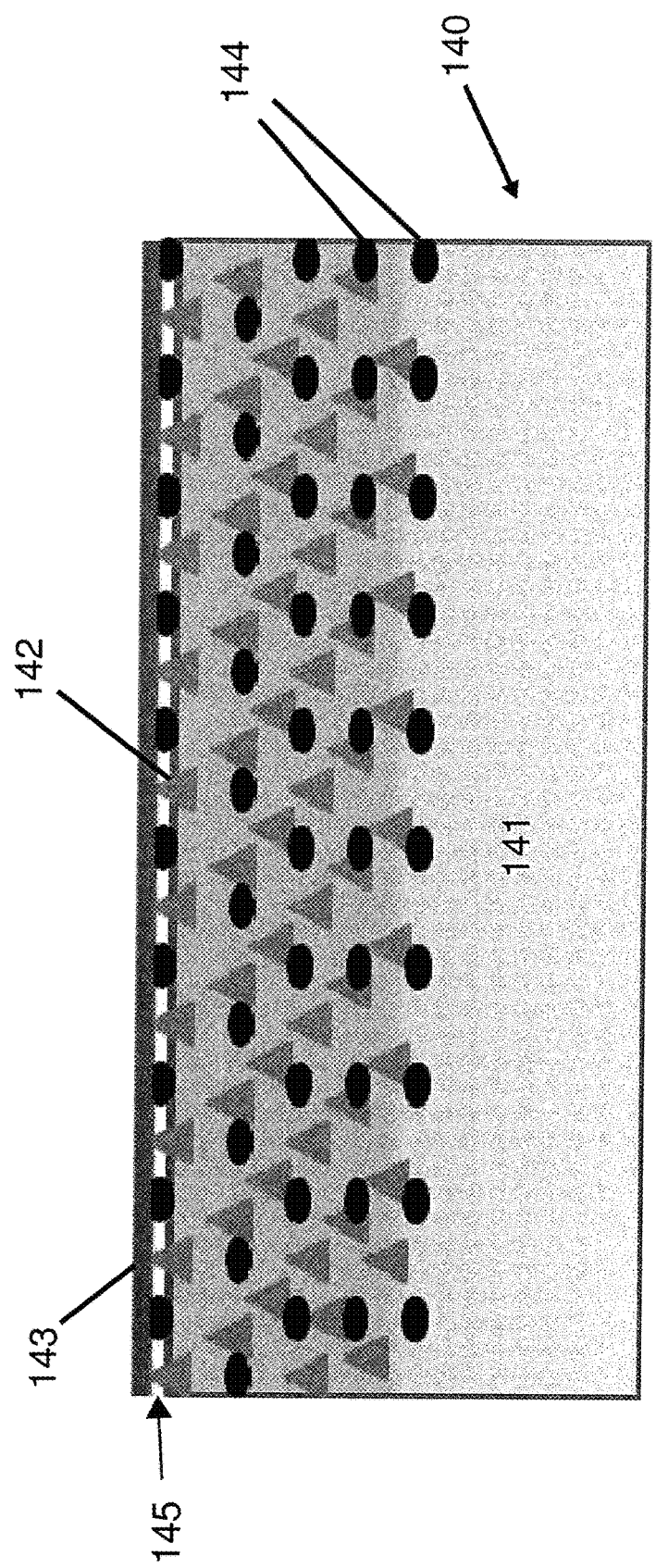
FIG. 6 is a cross-sectional view of yet another exemplary lubricated biocompatible metal device according to the present invention.

FIG. 6 is a cross-sectional view of an exemplary biocompatible lubricated metal device 140 according to another embodiment of the present invention. The lubricated biocompatible metal device 140 is similar to the devices 100 and 120 illustrated above in FIGS. 1 and 2, respectively. However, FIG. 4 illustrates a device 140 with a top layer 145 formed on the metal matrix 141 to cover the majority or the entire surface of the metal matrix 141 in addition to the solid lubricants 142 and any one or more additional solid lubricants 144, which form the solid-lubricated surface 143. As discussed above, the metal matrix 141 may be made of a plurality of suitable materials and could be formed to become progressively harder toward its top surface and reduce wear behavior of the device 140 further.

In an exemplary embodiment, the lubricated metal device 140 may be made of a Ti and zirconium (Zr) composition. The Ti—Zr composition will be fabricated such that progressively great concentrations of Zr are in layers or regions closer to the top layer 145. For example, in the middle the Zr may be less than 5%, but towards the top it may be between 90 and 100%. The top layer 145 may be formed by oxidizing the Zr that transitions to the surface of the metal matrix 141 into zirconium dioxide ($ZrO_2$). Such $ZrO_2$ layer may be formed like a continuous film covering the entire surface. In one embodiment, the metal matrix is oxidized simply by changing the amount of oxygen in the controlled environment after fabrication of the Ti—Zr-solid lubricant biocompatible device. Alternatively, the Ti—Zr-solid lubricant device is removed from the controlled oxygen environment of the LBMD process in order to perform the oxidation. The top layer of Zr can be oxidized via a number of methods, including, but not limited to, laser oxidation.

Figure 7:
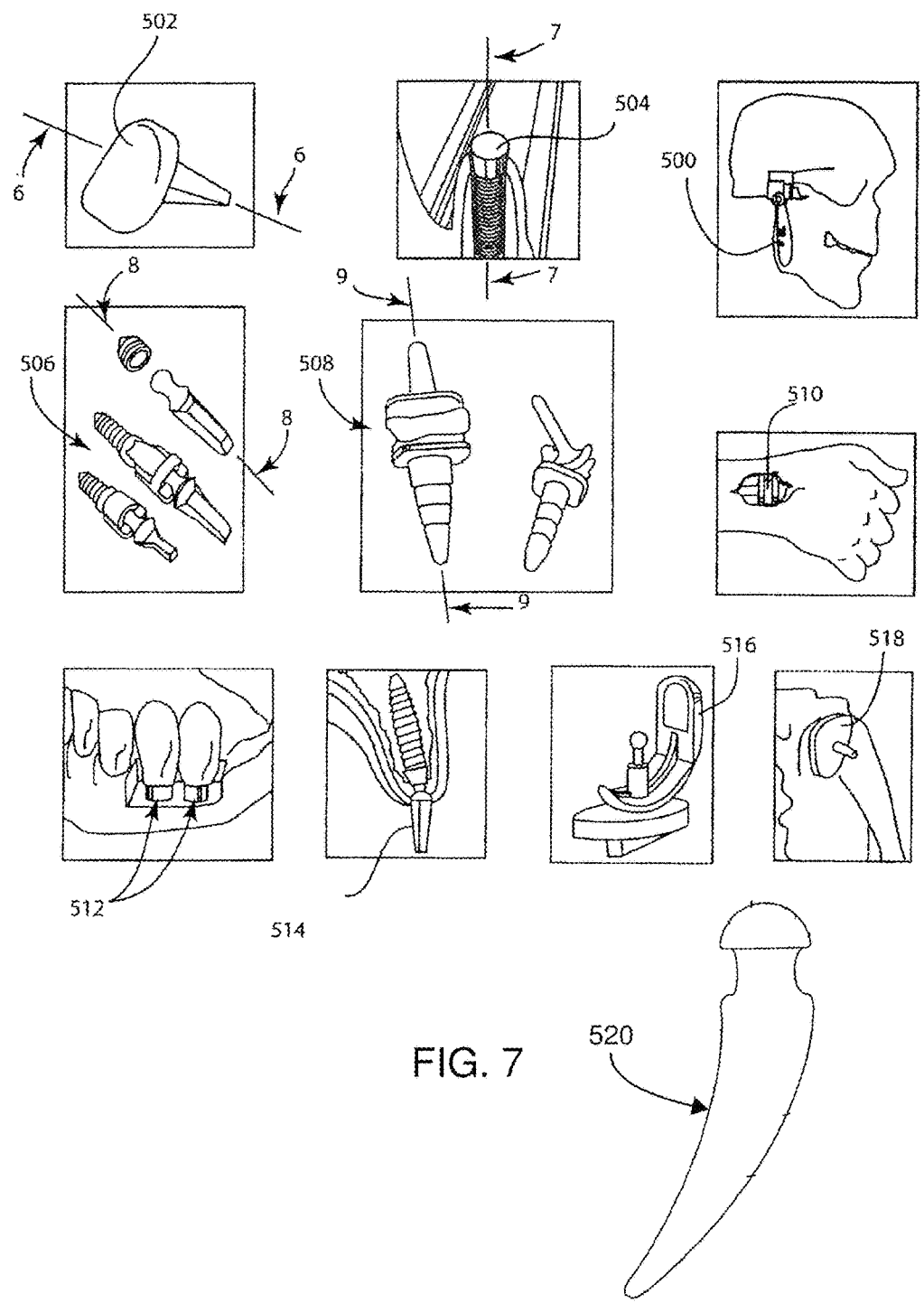
FIG. 7 illustrates, by way of example and not limitation, various possible devices in which the present invention might be embodied.

FIG. 7, which is based on that depicted in U.S. Pat. No. 7,666,522 to Justin et al., illustrates, by way of example and not limitation, various possible devices in which the present invention might be embodied. (It being recognized that U.S. Pat. No. 7,666,522 to Justin et al. does not show or describe a lubricated biocompatible metal device as contemplated herein.) The self-lubricated biocompatible metal device may be a medical implant that is shaped for a body part of patient for in vitro applications and in vivo applications. Devices shown in FIG. 7 include an implant for the temporomandibular joint 500 in situ, an implant for the great toe 502 (also generally representative of knee, wrist and spinal implants), a dental implant 504 in situ, articulating finger implants 506, thumb implants 508, a wrist implant 510 in situ, dental implants 512 in situ, a dental implant 514 in situ, a knee implant 516, a shoulder implant 518 in situ, and a hip implant 520.

Processed materials, including functionally or compositionally graded structures, according to the present invention have been evaluated for in vivo and ex vivo biocompatibility. Testing was conducted on commercially pure Ti (cp-Ti) and Ti6Al4V alloy to measure the performance of a solid-lubricating CaP reinforced Ti6Al4V matrix. Both cp-Ti and Ti6Al4V are widely used in biomedical devices. Granular tricalcium phosphate (TCP, $Ca_3(PO_4)_2$) powder, as a source for calcium phosphate (CaP), was ball milled and sieved to yield a particle size between 50 and 200 micron, cp-Ti and Ti6Al4V powders were also sieved between 50 and 150 micron size. Compositions were made by manually mixing cp-Ti powder with 0%, 3.3%, 6.8% and 10% TCP powder, and Ti6Al4V with 5% TCP by weight.

A 500 Watt continuous wave Nd-YAG laser, a scan speed of 7.6 mm/sec and laser power of 400 Watts was used to prepare the samples. Different size samples were fabricated using the method described herein. Samples with a 12 mm diameter were cut to 3 mm thickness discs, ground and polished to 1 micron with alumina, and then used for wear testing. Cylindrical samples of 8 mm diameter and 16 mm long were manufactured for compression testing.

Figure 8:
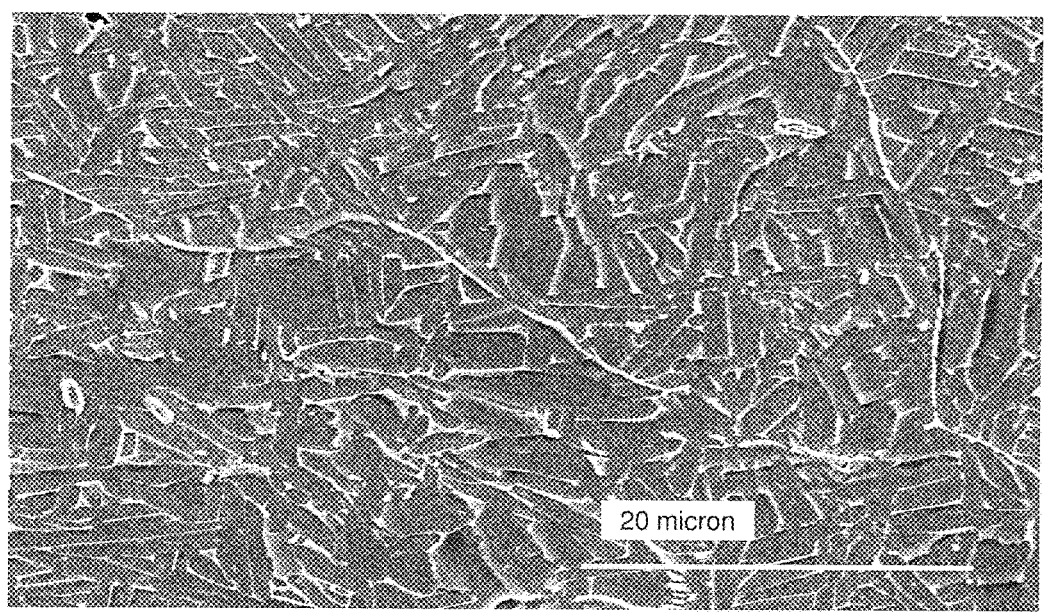
FIG. 8 shows the microstructure of polished samples of experiments of Ti6Al4V with 5% TCP composites.

Polished samples were etched to reveal the microstructure and a typical Ti6Al4V with 5% TCP is shown in FIG. 8. FIG. 8 shows that TCP is distributed mostly along the grain boundary areas. Similar features are also seen with all other compositions. Table 2 provided below summarizes microhardness and typical wear behavior of processed cp-Ti and Ti6Al4V composites with different amounts of TCP embedded within:

TABLE 2

| Sample | Hardness (HV) | Wear rate ($mm^3$/Nm) |
| --- | --- | --- |
| cp-Ti (pure) | 240 ± 7 | $2.85 \times 10^{-4}$ (±$1.82 \times 10^{-5}$) |
| cp-Ti with 3.3% TCP | 540 ± 20 | $7.41 \times 10^{-5}$ (±$2.54 \times 10^{-5}$) |
| cp-Ti with 6.8% TCP | 760 ± 30 | $3.44 \times 10^{-5}$ (±$2.30 \times 10^{-5}$) |
| cp-Ti with 10% TCP | 930 ± 50 | $2.32 \times 10^{-5}$ (±$1.04 \times 10^{-5}$) |
| Ti6Al4V with 5% TCP | 553 ± 8 | $6.36 \times 10^{-5}$ (±$0.78 \times 10^{-5}$) |
| CoCrMo alloy | 457 ± 12 | $1.06 \times 10^{-5}$ (±$1.06 \times 10^{-5}$) |

Table 2 demonstrates that increasing the amount of TCP also increases the hardness of the composites. For cp-Ti, addition of 10% TCP increased the hardness to almost 4-fold that is over 100% more than the hardness of CoCrMo alloy. For Ti6Al4V, 5% TCP addition increased the hardness over CoCrMo alloy. The average hardness of pure Ti6Al4V alloy is 360 HV. Compression tests revealed that both yield stress (YS) and ultimate tensile strength (UTS) increased due to the addition of TCP. For cp-Ti, average UTS increased from 1150 MPa (0% TCP) to 1380 MPa (6.8% TCP), with a variation of ~(+/−) 3% of UTS. Moreover, fatigue resistance of cp-Ti and Ti6Al4V samples without any TCP demonstrate no damage >$10^7$ cycles under rotating bending loading at 15 Hz with a stress ratio of 0.1 to a maximum stress level of 125% of their yield stress.

In addition, wear tests were performed using a Nanovea Series Tribometer (Microphotonics Inc., Calif. USA). Sample testing was conducted in linear reciprocating spherical ball on disc mode with a 10 mm stroke length. A 3 mm chrome steel ball (100Cr6, 58-63 HRC) with a five Newton load was used for the ball. Testing proceeded for 1000 m at 1200 mm/min. During the tribology testing, samples were submerged in simulated body fluid in a sample tray heated to 37° C. and the pH of the simulated body fluid was maintained at 7.4. Friction coefficients were measured during testing with a sampling rate of 100 milliseconds. Based on the resulting wear data, the progression of static coefficients of frictions and dynamic coefficients of frictions were analyzed. The static coefficient of friction was defined as the maximum coefficient of friction in the cycle. And, the dynamic coefficient of friction was calculated as the running average, excluding maximums and minimums. After testing, wear volume of the samples were measured and wear tracks were observed under a field emission scanning electron microscope (FESEM). Table 2 above shows the wear rates for different samples. Under similar conditions, the wear rate for CoCrMo alloy is $1 \times 10^{-5}$ $mm^3$/Nm. And for cp-Ti and/or Ti6Al4V, the wear rate is at least one order of magnitude more than the CoCrMo alloy.

Wear track images for the three selected compositions of cp-Ti with 0%, 3.3% and 6.8% TCP in it showed significant damage occurred for pure cp-Ti with extensive cracking in the metal matrix. Such a result is expected because Ti and its alloys are relatively soft metals and have poor wear resistance. For cp-Ti with 3.3% TCP, less surface damage and cracking is illustrated compared to the pure cp-Ti, and, unlike the pure cp-Ti, relatively smooth wear tracks are shown. However, cp-Ti with 6.8% TCP demonstrated the most significant improvement, showing no surface damage or visible wear tracks on its surface, and only CaP on the wear surface. Wear track analysis confirmed that CaP is acting as a solid lubricant minimizing any direct contact between the two metal surfaces during wear testing. In addition, most of the wear debris in this case is CaP instead of metal ions. The dynamic coefficient of friction also decreased with increasing CaP in the composite. Based on data, the addition of TCP in Ti can significantly increase wear resistance of the metal matrix and make it comparable to commercial CoCrMo alloy. And, such Ti-TCP composites not only eliminate the release of Co or Cr metal ions a body of patient during in vivo applications, but also minimizes the release of Ti ions due to wear because most of the wear debris consists of bio-friendly CaP.

Figure 9:
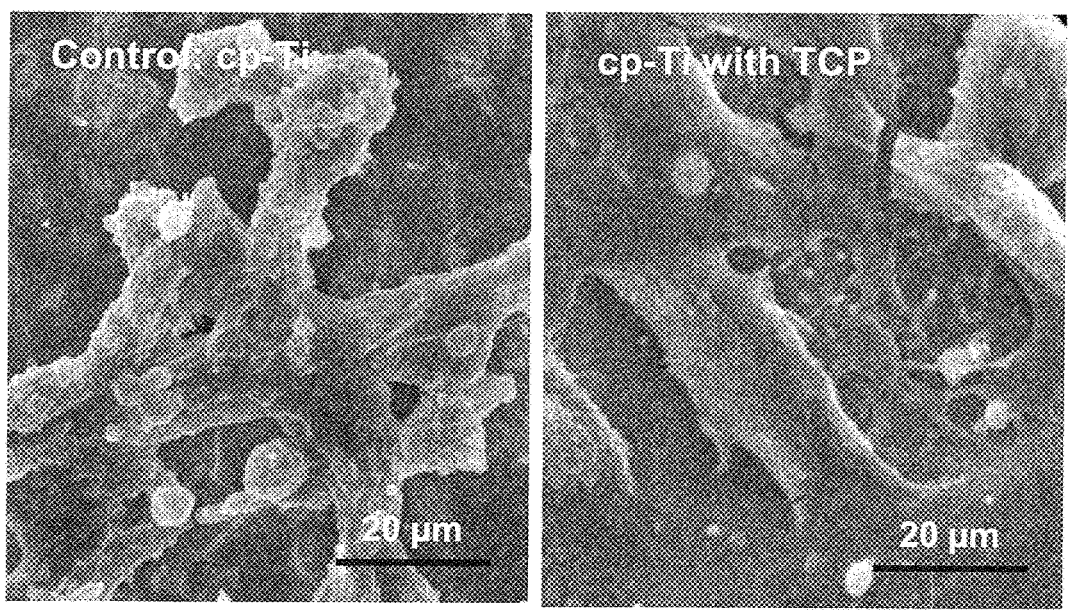
FIG. 9 shows cell adhesion after eleven days of incubation of testing on cp-Ti and a composite.

LBMD treated TCP-Ti composites are non-toxic and biocompatible. For testing of in vitro biocompatibility, human osteoblast (HOB) cells from human fetal bone tissue were used. All samples were sterilized by autoclaving at 121° C. for 20 min. Cells were seeded onto samples placed in six well plates and were cultured in McCoy's 5 A medium. Cells were maintained at 37° C. under an atmosphere of 5% $CO_2$ and 95% air. Culture medium was changed every two days in all plates. Samples were removed from culture after five and eleven days of incubation. FIG. 9 shows cell adhesion after eleven days of incubation of this testing. FIG. 9 illustrates that TCP-Ti composites show more flattened HOB cell morphology compared to control cp-Ti. Similar trends were also observed for cell proliferation and differentiation.

Figure 10:
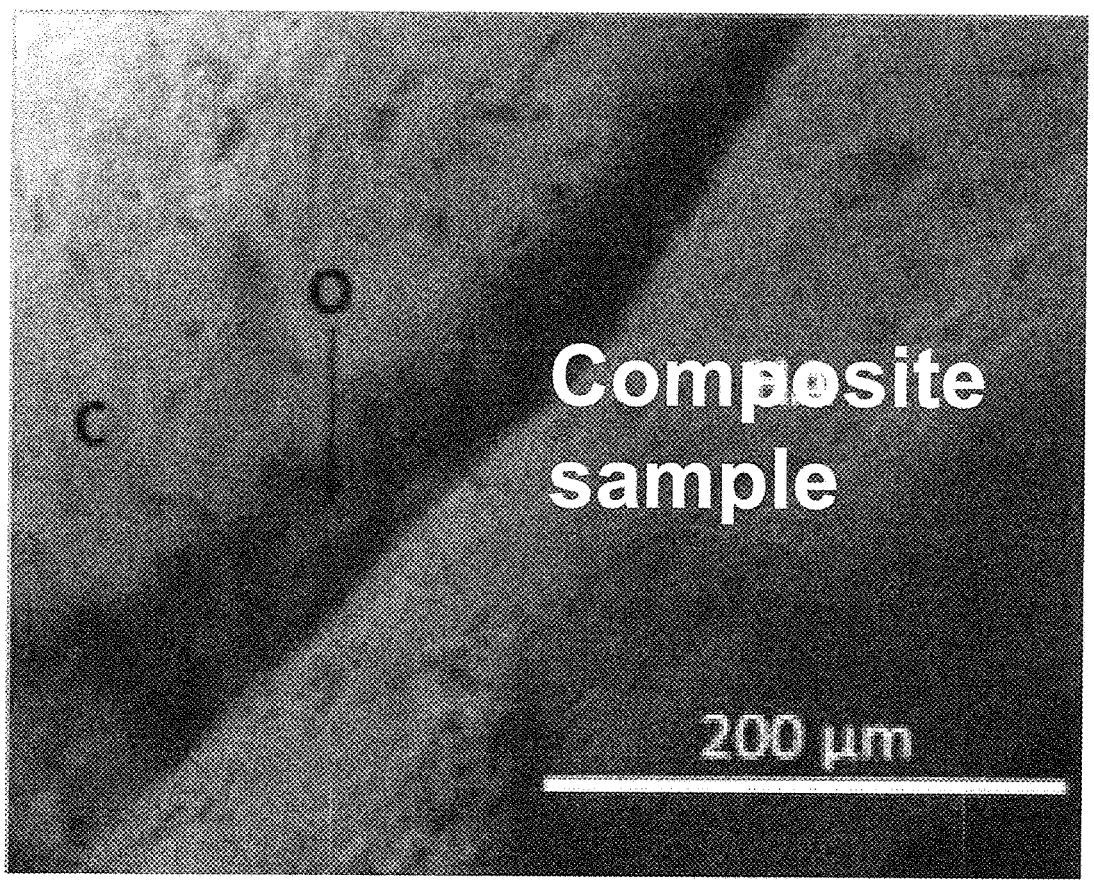
FIG. 10 shows in vivo cytotoxicity assessment at two weeks of implantation in the intramedullary defect of rat distal femur model.

Moreover, FIG. 10 shows in vivo cytotoxicity assessment at two weeks of implantation in the intramedullary defect of rat distal femur model. The region between the composite coating surface and old bone is shown to be rich in collagen and mesenchymal cells that differentiate to osteoblast phenotype and form bone, osteoid. FIG. 10 demonstrates no sign of toxicity from these coated samples which account for ~10% TCP in cp-Ti matrix.

Various embodiments disclosed herein are described as including a particular feature, structure, or characteristic, but every aspect or embodiment may not necessarily include the particular feature, structure, or characteristic. Further, when a particular feature, structure, or characteristic is described in connection with an embodiment, it will be understood that such feature, structure, or characteristic may be included in connection with other embodiments, whether or not explicitly described. Thus, various changes and modifications may be made to the provided description without departing from the scope or spirit of the disclosure.

Other embodiments, uses and features of the present disclosure will be apparent to those skilled in the art from consideration of the specification and practice of the inventive concepts disclosed herein. The specification and drawings should be considered exemplary only, and the scope of the disclosure is accordingly intended to be limited only by the following claims.

What is claimed is:

1. A biocompatible metal device, comprising:
    a substrate;
    a metal matrix on top of the substrate, the metal matrix having an interior portion proximate the substrate and an articulating surface extending away from the interior portion, wherein both the interior portion and the articulating surface are composed of a metal matrix material; and
    a solid lubricant excluding carbides as a plurality of discontinuous particles embedded in the metal matrix material, at least some of the discontinuous particles are at the articulation surface while others are proximate to the articulating surface, wherein the embedded discontinuous particles of the solid lubricant are releasable from the metal matrix material via the articulating surface during articulation of the biocompatible metal device to create a film of the solid lubricant covering at least a portion of the articulating surface, and wherein the created film of the solid lubricant during articulation reduces a friction coefficient of the metal matrix material at the articulating surface of the biocompatible metal device to protect the metal matrix material at the interior portion of the metal matrix.

2. The biocompatible metal device according to claim 1, wherein the biocompatible metal device is configured as a medical implant shaped for a body part of a patient for applications in vivo.

3. The biocompatible metal device according to claim 1, wherein the lubricated biocompatible metal device is configured as an industrial component.

4. The biocompatible metal device according to claim 1, wherein the solid lubricant is embedded into the metal matrix material by laser based metal deposition in a controlled oxygen environment.

5. The biocompatible metal device according to claim 4, wherein the metal matrix material includes aluminum, nickel, titanium, cobalt-chrome, tantalum, platinum, zirconium, niobium, stainless steel, or any alloys thereof.

6. The biocompatible metal device according to claim 5, wherein the material is an alloy of titanium, tantalum, and zirconium.

7. The biocompatible metal device according to claim 6 further comprising:
    a layer of zirconium dioxide on top of the articulating surface.

8. The biocompatible metal device according to claim 1, wherein the solid lubricant includes magnesium hydrosilicates, graphite, molybdenum disulfide, tungsten disulfide, hexagonal boron nitride, calcium phosphates, calcium sulphates, or polytetrafluoroethylene.

9. The biocompatible metal device according to claim 8 further comprising:
    one or more additional solid lubricants embedded in the metal matrix material.

10. The biocompatible metal device according to claim 9, wherein the one or more additional solid lubricants are different than the solid lubricant embedded in the metal matrix material, and wherein the one or more additional solid lubricants individually include magnesium hydrosilicates, graphite, molybdenum disulfide, tungsten disulfide, hexagonal boron nitride, calcium phosphates, calcium sulphates, polytetrafluoroethylene, alumina, or lead zirconate titanate.

11. The biocompatible metal device according to claim 1, wherein the biocompatible metal device is a biocompatible metal implant, and wherein the metal matrix material is composed of a titanium or titanium alloy.

12. The biocompatible metal implant of claim 11 further comprising:
a zirconium dioxide layer on top of the articulating surface.

13. The biocompatible metal device according to claim 1, wherein the biocompatible metal device is a biocompatible metal implant, and wherein the metal matrix is composed of a cobalt-chrome alloy.

14. The biocompatible metal implant of claim 13 further comprising:
a zirconium dioxide layer on top of the articulating surface.

15. The biocompatible metal device of claim 1, wherein the metal matrix material contains 5 to 25 wt. % of the solid lubricant.

16. A method for lubricating a metal device having:
a substrate;
a metal matrix on top of the substrate, the metal matrix having an interior portion proximate the substrate and an articulating surface extending away from the interior portion, wherein both the interior portion and the articulating surface are composed of a metal matrix material; and
a solid lubricant excluding carbides as a plurality of discontinuous particles embedded in the metal matrix material, at least some of the discontinuous particles are at the articulation surface while others are proximate to the articulating surface; and
wherein the method comprising:
releasing at least some of the embedded discontinuous particles of the solid lubricant from the metal matrix material via the articulating surface during articulation of the metal device;
with the released particles of the solid lubricant, creating a film of the solid lubricant covering at least a portion of the articulating surface during articulation, the created film of the solid lubricant reducing a friction coefficient of the metal matrix material at the articulating surface of the biocompatible metal device to protect the metal matrix material at the interior portion of the metal matrix; and
replenishing the created film with additional embedded discontinues particles of the solid lubricant during articulation.

17. The method for lubricating the metal device according to claim 16, wherein the particles of the solid lubricant are embedded by laser based metal deposition in a controlled oxygen environment.

18. The method for lubricating the metal device according to claim 17, wherein the metal matrix material includes aluminum, nickel, titanium, cobalt-chrome, tantalum, platinum, zirconium, niobium, stainless steel, or any alloys thereof.

19. The method for lubricating the metal device according to claim 18, wherein the metal matrix material is an alloy of titanium and zirconium.

20. The method for lubricating the metal device according to claim 19, further comprising:
forming a layer on the articulating surface by oxidizing the zirconium into zirconium dioxide.

21. The method for lubricating the metal device according to claim 16, wherein the solid lubricant includes magnesium hydrosilicates, graphite, molybdenum disulfide, tungsten disulfide, hexagonal boron nitride, calcium phosphates, calcium sulphates, polytetrafluoroethylene, alumina, or lead zirconate titanate.

22. The method for lubricating the metal device according to claim 21, wherein:
the metal device includes one or more additional solid lubricants embedded into the metal matrix material.

23. The method for lubricating the metal device according to claim 22, wherein the one or more additional solid lubricants are different than the solid lubricant embedded in the metal matrix material, and wherein the one or more additional solid lubricants individually include magnesium hydrosilicates, graphite, molybdenum disulfide, tungsten disulfide, hexagonal boron nitride, calcium phosphates, calcium sulphates, polytetrafluoroethylene, alumina, or lead zirconate titanate.

* * * * *